United States Patent [19]

Schroeder

[11] 4,119,634
[45] Oct. 10, 1978

[54] BIS-BENZOXAZOLYL-COMPOUNDS

[75] Inventor: Josef Schroeder, Cologne, Germany

[73] Assignee: Bayer Aktiengesellschaft, Leverkusen, Germany

[21] Appl. No.: 823,133

[22] Filed: Aug. 9, 1977

[30] Foreign Application Priority Data

Aug. 11, 1976 [DE] Fed. Rep. of Germany ....... 2636090

[51] Int. Cl.² .......................................... C07D 263/62
[52] U.S. Cl. ....................... 260/307 D; 260/45.8 NT; 260/308 B
[58] Field of Search .................................... 260/307 D

[56] References Cited

U.S. PATENT DOCUMENTS 3,926,969  12/1975  Fleck et al. ...................... 260/240.1

Primary Examiner—Raymond V. Rush
Attorney, Agent, or Firm—Plumley & Tyner

[57] ABSTRACT

Bis-benzoxazolyl compounds of the formula

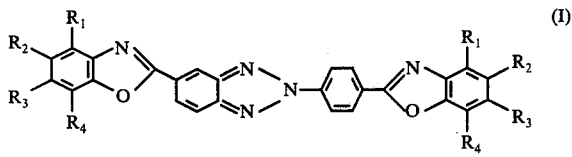

(I)

wherein $R_1$, $R_2$, $R_3$ and $R_4$ independently of one another denote hydrogen, halogen, optionally substituted $C_1$–$C_8$-alkyl, optionally substituted $C_1$–$C_4$-alkoxy, aralkyl, aryl, carboxyl, cyano, $C_1$–$C_4$-alkoxycarbonyl, carboxamide which is optionally substituted by $C_1$–$C_4$-alkyl, aryl or aralkyl, or $C_1$–$C_4$-alkylsulphonyl, or 2 adjacent radicals $R_1$–$R_4$ represent a fused, optionally substituted aromatic or hydroaromatic ring, are suitable for the brightening of plastics and of polyester fibres.

2 Claims, No Drawings

BIS-BENZOXAZOLYL-COMPOUNDS
substituted

The invention relates to bis-benzoxazolyl compounds of the formula

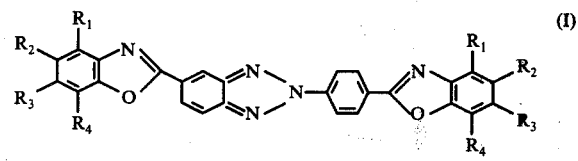

wherein $R_1$, $R_2$, $R_3$ and $R_4$ independently of one another denote hydrogen, halogen, optionally substituted $C_1$–$C_8$-alkyl, optionally substituted $C_1$–$C_4$-alkoxy, aralkyl, aryl, carboxyl, cyano, $C_1$–$C_4$-alkoxycarbonyl, carboxamide which is optionally substituted by $C_1$–$C_4$-alkyl, aryl or aralkyl, or $C_1$–$C_4$-alkylsulphonyl, or 2 adjacent radicals $R_1$–$R_4$ represent a fused, optionally substituted aromatic or hydroaromatic ring, their preparation and their use as optical brighteners.

The compounds (I) are prepared in a manner which is in itself known by reacting o-aminophenols of the formula

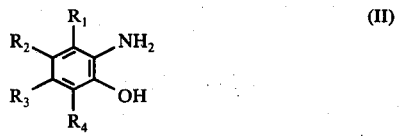

wherein $R_1$, $R_2$, $R_3$ and $R_4$ possess the abovementioned meaning, with 2-phenylbenztriazolyl compounds of the formula

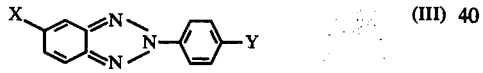

wherein

X and Y denote cyano, carboxyl, $C_1$–$C_4$-alkoxycarbonyl or halogenocarbonyl.

Compounds of the formula (III) in which X or X and Y denote cyano are appropriately reacted with the aminophenols (II) by heating in polyphosphoric acid and nitrogen at 100°–200° C to give the compounds (I). Carboxylic acids, carboxylic acid esters and carboxylic acid chlorides of the formula (III) are appropriately reacted with the aminophenols (II) in inert solvents, such as high-boiling ethers or chlorinated aromatic compounds, and in this case an anilide first forms and this is cyclised in the presence of boric acid to give the benzoxazolyl compound (I).

Examples of suitable compounds (II) are 2-aminophenol, 2-amino-4-methylphenol, 2-amino-5-methylphenol, 2-amino-4,5-dimethylphenol, 2-amino-4,6-dimethylphenol, 2-amino-4-octylphenol, 2-amino-4-tert.-butylphenol, 2-amino-4-phenylphenol, 2-amino-4-(1-methyl-1-phenethyl)-phenol, 2-amino-4-cyclohexylphenol, 1,1,3,3-tetramethyl-5-hydroxy-6-aminoindane, 2-amino-4-chlorophenol, 2-amino-4,5-dichlorophenol, 2-amino-4-ethoxycarbonylphenol, 2-amino-4-ethylsulphonylphenol, 2-amino-1-hydroxynaphthalene and 1-amino-2-hydroxy-5,6,7,8-tetrahydronaphthalene.

The compound of the formula (III) in which X and Y represent carboxyl can be prepared in various ways, for example by cyclising 2,4-diamino-4'-methoxycarbonylazobenzene to give 2-(4-methoxycarbonylphenyl)-5-aminobenzotriazole, nitrosating the latter, carrying out a Sandmeyer reaction to give the 5-cyano compound and hydrolysing this compound; by cyclising 2-nitro-4-methyl-4'-methoxycarbonylazobenzene with triethyl phosphite to give 2-(4-methoxycarbonylphenyl)-5-methylbenztriazole, hydrolysing the ester group and oxidising the methyl group to the carboxyl group; by a corresponding reaction with 2-nitro-4-carboxy-4'-methoxycarbonylazobenzene and triethyl phosphite and subsequent hydrolysis of the reaction product, or by oxidation of 2-(4-methylphenyl)-5-methylbenztriazole.

The compound of the formula (III) in which X and Y represent cyano is prepared by oxidative cyclisation of 2,4-diamino-4'-nitroazobenzene to give the benztriazole derivative, reduction of the nitro group, diazotisation of the amino groups and introduction of the cyano groups by a Sandmeyer reaction.

Preferred compounds within the formula (I) are benztriazolyl compounds of the formula

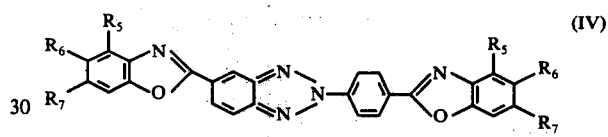

wherein $R_5$ denotes hydrogen or conjointly with $R_6$ denotes —$CH_2$—$CH_2$—$CH_2$— or —$CH$=$CH$—$CH$=• $CH$—, $R_6$ denotes hydrogen, $C_1$–$C_8$ alkyl, phenyl, phenyl—$C_1$–$C_4$— alkyl, chlorine, $C_1$–$C_4$-alkoxycarbonyl or $C_1$–$C_4$-alkylsulphonyl, or, conjointly with $R_5$, denotes —$CH_2$—$CH_2$—$CH_2$—$CH_2$— or —$CH$=$CH$—$CH$=$CH$—, or, conjointly with $R_7$, denotes a 5-membered or 6-membered hydroaromatic ring which has a total of not more than 10 C atoms and is optionally monosubstituted to tetrasubstituted by $C_1$–$C_4$-alkyl, and $R_7$ denotes hydrogen, methyl or chlorine or, conjointly with $R_6$, denotes a 5-membered or 6-membered hydroaromatic ring which has a total of not more than 10 C atoms and is optionally monosubstituted to tetrasubstituted by $C_1$–$C_4$-alkyl.

The compounds (I) as a rule have high melting points and are sparingly soluble and, because of their ability to remit radiation absorbed in the UV range in the blue range of the visible spectrum, are suitable as optical brighteners. Surprisingly, excellent brightening effects are achieved in particular in plastics, such as polyethylene, polypropylene, polystyrene, polyvinyl chloride, polycarbonates, polymethyl methacrylate and cellulose acetates. Fibres made of polyethylene terephthalate can likewise be brightened from an aqueous liquor and by the spinning-in process. The fastness to light of the brightening effects is very good. The optical brighteners of the formula (I) are generally used in an amount of 0.001 to 0.1% relative to the substrate to be brightened.

EXAMPLE 1

5 g of 2-amino-4-methylphenol are dissolved in 50 ml of hot dioxane. 10 ml of pyridine and a suspension of 6.4 g of 2-(4-chlorocarbonylphenyl)-5-chlorocarbonylbenzotriazole in 70 ml of hot dioxane are added to this solution. The mixture is boiled under reflux for one hour, 100 ml of methanol are added and the mixture is cooled. The crystals of the bisanilide which have separated out are filtered off, dried and heated, without further purification, in 100 ml of diphenyl ether in the presence of 1 g of boric acid for 4 hours under reflux. After cooling, 100 ml of ethanol are added and the crude product which has precipitated out is filtered off. After recrystallising twice from o-dichlorobenzene in the presence of bleaching earth and active charcoal, 3.5 g of the compound of the formula

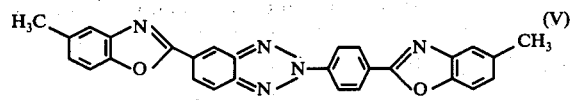 (V)

are obtained.

The following compounds were obtained in an analogous manner:

Table 1

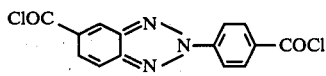 (VI)

| Example | A |
|---------|---|
| 2 | (H₃C)₃—C— (benzoxazole) |
| 3 | (benzoxazole) |
| 4 | H₃C, CH₃ / H₃C, CH₃ (tetramethyl-benzoxazole) |
| 5 | H₃C—C(CH₃)—H₂C—C(CH₃)(CH₃)— (benzoxazole) |
| 6 | phenyl-C(CH₃)₂— (benzoxazole) |
| 7 | H₅C₂O₂C— (benzoxazole) |
| 8 | H₃C— (benzoxazole) |
| 9 | (naphthoxazole) |

The 2-(4-chlorocarbonylphenyl)-5-chlorocarbonylbenzotriazole used in Examples 1 to 9 was prepared in the following way: p-aminobenzoic acid methyl ester is diazotised in the customary manner and the diazo compound is coupled with m-phenylenediamine. The resulting crude azo dyestuff is oxidised in hot pyridine with Cu-II acetate to give 2-(4-methoxycarbonylphenyl)-5-aminobenztriazole with a melting point of 240° C, 135 g of this amine are dissolved in 375 ml of concentrated sulphuric acid and diazotised at 15° to 20° C with nitrosylsulphuric acid. The diazonium salt solution is discharged onto 2.5 kg of ice; the diazonium salt is filtered off and suspended in 800 ml of ice water. This suspension is added in small portions to a solution of 50 g of copper-I cyanide, 75 g of sodium cyanide, 500 ml of water and 250 ml of dimethylformamide. A brown product separates out, with vigorous evolution of gas, and this product can be purified by recrystallisation from o-dichlorobenzene and dimethylformamide; melting point 265° C, blue-fluorescent. The product has the formula

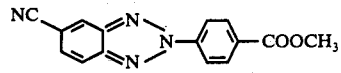

and is subjected to alkaline saponification in aqueous glycol monomethyl ether. The product of the formula ClOC—⟨benzotriazole⟩—N—⟨phenyl⟩—COCl which melts at 146°–148° C is obtained by boiling in a large excess of thionyl chloride.

EXAMPLE 10

300 g of polyphosphoric acid (85% of P₂O₅) are heated to 100° C under nitrogen. 27.8 g of 2-(4-methoxycarbonylphenyl)-5-cyanobenztriazole and 26 g of purified 3-amino-4-hydroxytoluene are introduced successively, whilst stirring, and the mixture is heated to 210° C in the course of 2 hours. This temperature is maintained for one hour and the melt is introduced into 1.5 l of water. The crude product is filtered off and stirred into hot water, the mixture is neutralised with sodium carbonate solution and the product is filtered off again. The crude product (42.5 g) is dried and recrystallised twice from o-dichlorobenzene, active charcoal and bleaching earth being added. This gives a product which is identical with the product obtained according to Example 1.

The following compounds of the formula VI were obtained in an analogous manner:

Table 2

| Example | A |
|---------|---|
| 11 | Cl— (benzoxazole) |
| 12 | Cl—, Cl— (dichloro-benzoxazole) |
| 13 | H₃C—, H₃C— (dimethyl-benzoxazole) |
| 14 | H₅C₂—O₂S— (benzoxazole) |

EXAMPLE 15

Using a liquor ratio of 1:40, 5 g of polypropylene yarn are dyed at the boil for one hour in the presence of an anionic dispersing agent with 5 mg of the brightener from Example 1. After rinsing and drying, the yarn shows a very good brightening effect with very good fastness to light.

EXAMPLE 16

Using a liquor ratio of 1:40, 5 g of polypropylene fabric are dyed at the boil for one hour in the presence of an alkyl polyglycol ether and acetic acid (0.1 g) with 5 mg of the brightener from Example 1 (1 g dissolved in 1 l of dimethylformamide). After rinsing and drying, a fabric which displays an outstanding brightening effect with very good fastness to light is obtained.

EXAMPLE 17

100 g of granulated polypropylene are mixed, at 240° to 260° C, with 2 g of titanium dioxide and 100 mg of the brightener from Example 4 and the mixture is processed in an extruder. The polypropylene displays a very good brightening effect of outstanding fastness to light. Similar results are obtained with polyethylene and polystyrene at 200° to 220° C and with polycarbonate at about 300° C.

I claim:
1. A bis-benzoxazolyl compound of the formula

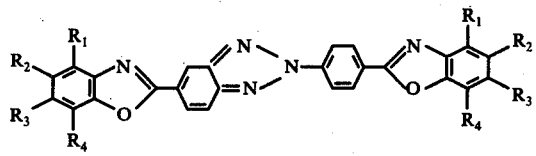

wherein $R_1$, $R_2$, $R_3$ and $R_4$ independently of one another are hydrogen; halogen; $C_1-C_8$-alkyl; $C_1-C_4$-alkoxy; phenyl; phenyl-$C_1-C_4$-alkyl; carboxyl; cyano; $C_1-C_4$-alkoxycarbonyl; $C_1-C_4$-alkylsulfonyl; carboxamide, or carboxamide substituted by $C_1-C_4$-alkyl, phenyl or phenyl-$C_1-C_4$-alkyl; or two adjacent radicals $R_1-R_4$ taken together with the carbon atoms to which they are attached represent a benzene, cyclohexene or 3,3,5,5-tetramethylcyclopentene ring.

2. A bis-benzoxazolyl compound of claim 1 of the formula

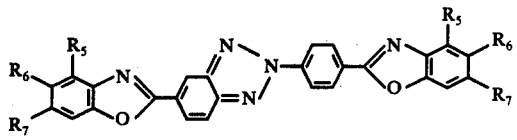

wherein $R_5$ is hydrogen;
$R_6$ is hydrogen, $C_1-C_8$-alkyl, phenyl, phenyl-$C_1-C_4$-alkyl, chlorine, $C_1-C_4$-alkoxycarbonyl or $C_1-C_4$-alkylsulfonyl;
$R_7$ is hydrogen, methyl or chlorine; or
$R_5$ and $R_6$ conjointly are —$CH_2CH_2CH_2CH_2$— or —CH=CH—CH=CH—; or
$R_6$ and $R_7$ conjointly are —$C(CH_3)_2$ — $CH_2$ — $C(CH_3)_2$ —.

* * * * *